United States Patent
Lee et al.

(10) Patent No.: US 8,416,101 B2
(45) Date of Patent: Apr. 9, 2013

(54) AIR CONDITIONER AND METHOD FOR CONTROLLING A LIGHT UNIT HAVING A PREDETERMINED COLOR TEMPERATURE

(75) Inventors: Ju Youn Lee, Seoul (KR); Baik Young Chung, Seoul (KR); Jae Dong Jang, Seoul (KR)

(73) Assignee: LG Electronics Inc., Seoul (KR)

( * ) Notice: Subject to any disclaimer, the term of this patent is extended or adjusted under 35 U.S.C. 154(b) by 667 days.

(21) Appl. No.: 12/685,211

(22) Filed: Jan. 11, 2010

(65) Prior Publication Data

US 2010/0175405 A1 Jul. 15, 2010

(30) Foreign Application Priority Data

Jan. 12, 2009 (KR) .................. 10-2009-0002157

(51) Int. Cl.
G08B 21/00 (2006.01)
(52) U.S. Cl.
USPC .............. 340/999; 340/540; 362/231; 600/27
(58) Field of Classification Search .................. 340/500, 340/540, 999, 573.1; 362/230–234; 600/27
See application file for complete search history.

(56) References Cited

U.S. PATENT DOCUMENTS

2003/0231495 A1 12/2003 Searfoss, III

FOREIGN PATENT DOCUMENTS

| JP | 2003-004278 | 1/2003 |
| JP | 2006-194563 | 7/2006 |
| JP | 2007-044201 | 2/2007 |
| JP | 2008-241089 | 10/2008 |
| WO | WO 2009/108228 | 9/2009 |

OTHER PUBLICATIONS

European Search Report dated May 7, 2010.
Korean Office Action dated Jan. 17, 2011 (Application No. 10-2009-0002157).

*Primary Examiner* — Jeffery Hofsass
(74) *Attorney, Agent, or Firm* — KED & Associates LLP

(57) ABSTRACT

An air conditioner and a method for controlling an air conditioner are provided. The air conditioner includes an air-conditioning device that air-conditions an indoor space, a lighting device that illuminates the indoor space, an input device that receives signals to operate the air-conditioning device and for selecting a sleep mode, and a controller that controls the lighting device and the air-conditioning device. When the input device receives the signal for selecting the sleep mode, the lighting device is controlled to sequentially perform a sleep entry operation in which the indoor space is illuminated to have a predetermined luminance and color temperature for a predetermined time, a sleep operation in which the indoor space is illuminated to have a predetermined luminance and color temperature until a wakeup time, and a wakeup operation in which the indoor space is illuminated to have a predetermined luminance and color temperature.

20 Claims, 4 Drawing Sheets

AIR CONDITIONER AND METHOD FOR CONTROLLING A LIGHT UNIT HAVING A PREDETERMINED COLOR TEMPERATURE

CROSS-REFERENCE TO RELATED APPLICATIONS

The present application claims priority under 35 U.S.C. 118B and 35 U.S.C. 365 to Korean Patent Application No. 10-2009-0002157 (filed on Jan. 12, 2009), which is hereby incorporated by reference in its entirety.

BACKGROUND

The present disclosure relates to an air conditioner and, more particularly, to an air conditioner that has a lighting illuminating an indoor space for user's comfortable sleep and a method for controlling the air conditioner.

An air conditioner is an appliance that cools or heats an indoor space. However, the air conditioners of related arts have a limitation in that they cannot fulfill a variety of requirements of sleepers.

SUMMARY

Embodiments provide an air conditioner having a variety of functions and a method for controlling the air conditioner.

Embodiments also provide an air conditioner that can allow a sleeper to more efficiently get a sleep and a method for controlling the air conditioner.

In one embodiment, an air conditioner includes an air-conditioning unit comprising a variety of components for air-conditioning of an indoor space; an lighting unit for illuminating the indoor space; an input unit receiving signals for operating the air-conditioning unit and signals for selecting a sleep mode; and a control unit controlling such that, when the input unit receives the signal for selecting the sleep mode, the lighting unit sequentially performs a sleep entry operation where the indoor space is illuminated to have a predetermined sleep entry luminance by light having a predetermined sleep entry color temperature for a predetermined sleep entry operation time, a sleep operation where the indoor space is illuminated to have a predetermined sleep luminance by light having a predetermined sleep color temperature unit it reaches a predetermined wakeup time, and a wakeup operation where the indoor space is illuminated to have a predetermined wakeup luminance by light having a predetermined wakeup color temperature.

In another embodiment, a method for controlling an air conditioner includes allowing a lighting unit to illuminate an indoor space with a first predetermined luminance using light having a first predetermined color temperature; allowing the lighting unit to illuminate the indoor space using light having the first predetermined color temperature such that a luminance is gradually reduced from the first predetermined luminance to a second predetermined luminance; allowing the lighting unit to illuminate the indoor space with the second predetermined luminance using light having the first predetermined color temperature; and allowing the lighting unit to illuminate the indoor space using light having the second predetermined color temperature such that a luminance is gradually increased from the second predetermined luminance to a third predetermined luminance.

According to the embodiments, the air conditioner has a variety functions and allows the user to efficiently have a sleep and wakeup.

The details of one or more embodiments are set forth in the accompanying drawings and the description below. Other features will be apparent from the description and drawings, and from the claims.

DETAILED DESCRIPTION OF THE EMBODIMENTS

Reference will now be made in detail to the embodiments of the present disclosure, examples of which are illustrated in the accompanying drawings.

Figure 1:
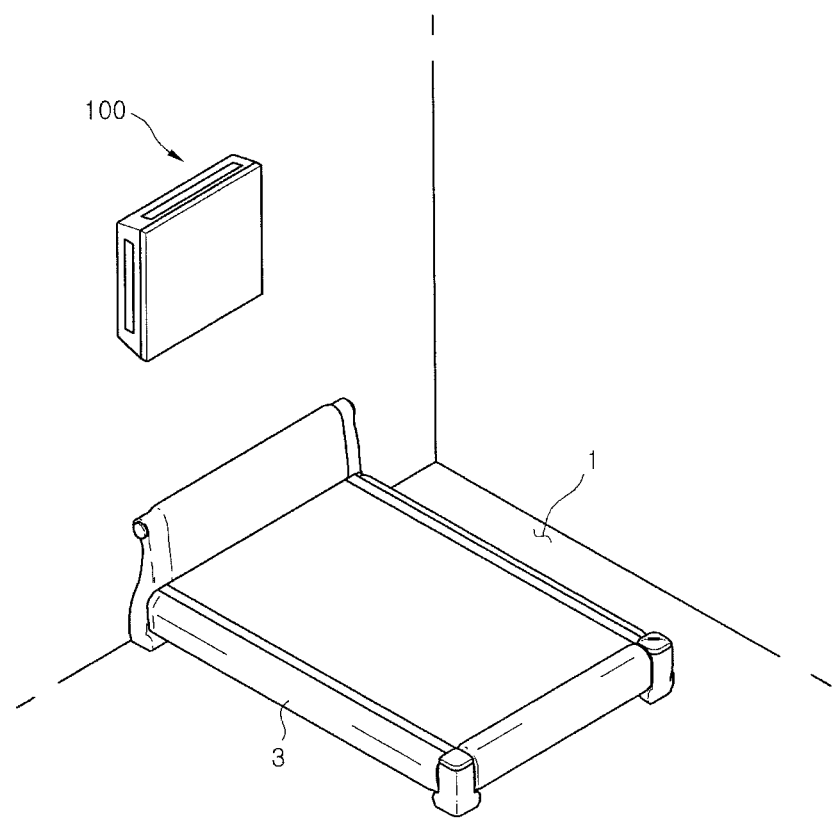
FIG. 1 is a perspective view of an air conditioner according to an embodiment.
Figure 2:
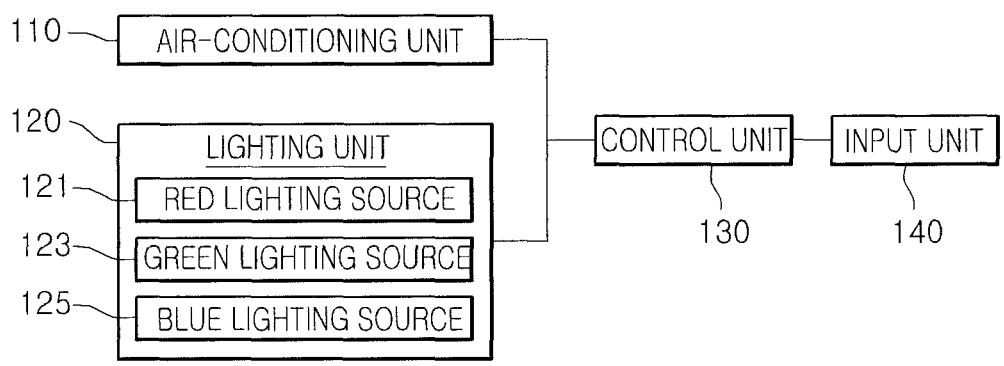
FIG. 2 is a block diagram of an air conditioner according to an embodiment.

FIG. 1 is a perspective view of an air conditioner according to an embodiment and FIG. 2 is a block diagram of an air conditioner according to an embodiment.

Referring first to FIG. 1, an air conditioner of an embodiment may be installed at a side of an indoor space 1. In FIG. 1, the air conditioner 100 is installed such that a lighting unit 120 can illuminate a bed 3 installed in a bedroom where a user get a sleep. In addition, the air conditioner 100 is installed on a wall surface above a head portion of the bed 3.

Referring to FIG. 2, the air conditioner 100 includes an air-conditioning unit 도 110, a lighting unit 120, an input unit 130, and a control unit 140. The air-conditioning unit 110 includes a variety of components such as a compressor, an indoor unit, and the like for air-conditioning a bedroom. Since a structure of the air-conditioning unit is well known in the art, detailed description of the air-conditioning unit will be omitted herein.

The lighting unit 120 includes a red lighting source 121, a green lighting source 123, and a blue lighting source 125. The red, green, and blue lighting sources 121, 123, and 125 generate red, green, and blue lights, respectively. For example, light emitting diodes (LEDs) may be used as the red, green, and blue lighting sources 121, 123, and 125. The lighting unit 120 illuminates the indoor space 1 adjacent to the air conditioner 100. At this point, the lighting unit 120 illuminates the indoor space 1 so that the user can efficiently get a sleep and wake up. This will be described later.

The input unit 130 signals such as, for example, a signal for setting a cooling temperature and/or a signal for controlling an air volume. In addition, the input unit 130 receives signal for setting a sleep mode. For example, the input unit 130 receives signals for selecting the sleep mode, and setting a sleep time in an hour or minute unit.

The control unit 140 controls the air-conditioning unit 110 in accordance with the signal input to the input unit 130. That is, the control unit 140 controls the air-conditioning unit 110 in accordance with the air-conditioning temperature and time input to the input unit 130.

Further, when the input unit 130 receives a signal for selecting the sleep mode and signals for setting a sleep time, i.e., a sleep entry time and a wakeup time, the control unit 140 controls such that the lighting unit 120 performs a sleep preparation operation, a sleep entry operation, a sleep operation, a wakeup preparation operation, and a wakeup operation. In more detail, when the input unit 130 receives the signal for selecting the sleep mode and the signals for setting a sleep time, i.e., a sleep entry time and a wakeup time, the control unit 140 controls such that the lighting unit 120 performs the sleep preparation operation before the sleep time initiates, i.e., unit it reaches the sleep entry time. Further, when it reaches the sleep entry time, the control unit 140 controls such that the lighting unit 120 performs the sleep entry operation for the sleep entry time. When the sleep entry time has elapsed, the control unit 140 controls such that the lighting unit 120 performs the sleep operation until it reaches the wakeup time. When it reaches the wakeup time, the control unit 140 controls such that the lighting unit performs the wakeup preparation operation for the wakeup preparation time. When the wakeup preparation time has elapsed, the control unit 140 controls such that the lighting unit 12 performs the wakeup operation.

In the sleep preparation operation, the indoor space 1 is illuminated to have a first predetermined luminance L1 by light having a first predetermined color temperature K1. In the sleep entry operation, the indoor space 1 is illuminated by the light having the first predetermined color temperature K1 such that the luminance is gradually reduced from the first predetermined luminance L1 to a second predetermined luminance L2. In the sleep operation, the indoor space 1 is illuminated by the light having the first predetermined color temperature K1 to have the second predetermined luminance L2 until it reaches the wakeup time. In the wakeup preparation operation, the indoor space 1 is illuminated by the light having a second predetermined color temperature K2 such that the luminance is gradually increased from the second predetermined luminance L2 to a third predetermined luminance L3. Finally, in the wakeup operation, the indoor space 1 is illuminated to have the third predetermined luminance L3 by the light having the second predetermined color temperature K2. The first predetermined color temperature K1 is a color temperature allowing the user to efficiently get a sleep. The second predetermined color temperature K2 is a color temperature allowing the user to efficiently wakeup. In addition, the first and second predetermined luminances L1 an L2 are luminances allowing the user to efficiently get the sleep. The third predetermined luminance L3 is a luminance allowing the user to efficiently wakeup. For example, the first predetermined color temperature K1 may be 2000-4000K, preferably, 3000K. In addition, the second predetermined color temperature K2 may be 4000-6000K, preferably 5000K. The first and second predetermined color temperatures K1 and K2 are determined by adjusting a ratio of R, G, and B values of the red, green, and blue lighting sources 121, 123, and 125. Further, the first predetermined luminance L1 may be 1-100 Lux, preferably 10 Lux. The second predetermined luminance L2 may be 0.01-1 Lux, preferably, 0.1 Lux. The third predetermined luminance L3 may be 10-1000 Lux, preferably 100 Lux. However, the first and second predetermined color temperature K1 and K2 and the first to third predetermined luminances L1, L2, and L3 are set to satisfy the following conditions.

(1) First and second predetermined color temperature

K1<K2

(2) First to third predetermined luminances

L2<L1<L3

That is, the second predetermined color temperature K2 is set to be greater than the first predetermined color temperature K1. The second predetermined luminance L2 is set to be less than the first predetermined luminance L1. The third predetermined luminance L3 is set to be greater than the first predetermined luminance L1.

Meanwhile, the sleep entry operation time is about 5 minutes and the wakeup preparation operation time is about 30 minutes. The sleep entry operation time and the wakeup preparation time may be 10 minutes.

The following will describe an air conditioner according to another embodiment.

Figure 3:
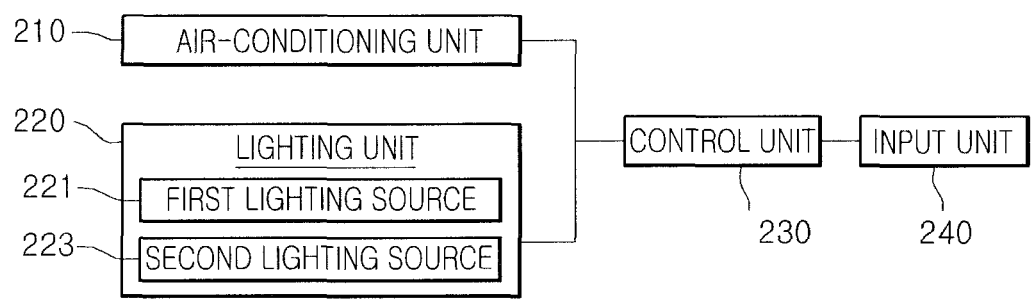
FIG. 3 is a block diagram of an air conditioner according to another embodiment.

FIG. 3 is a schematic diagram of an air conditioner according to another embodiment.

Referring to FIG. 3, an air conditioner of this embodiment includes an air-conditioning unit 210, a lighting unit 220, an input unit 230, and a control unit 240. Since the air-conditioning unit 210, input unit 230, and control unit 240 are same as those of the previously described embodiment, detailed description thereof will be omitted herein. The lighting unit 220 includes first and second lighting sources 221 and 223. Here, the first lighting source 221 generates light having a first predetermined color temperature K1 and the second lighting source 221 generates light having a second predetermined color temperature K2. For example, the first lighting source 221 may be an incandescent lamp generating light having a color temperature of 2000-4000K and the second lighting source 223 may be a fluorescent lamp generates light having a color temperature of 4000-6000K.

The following will describe a method for controlling an air conditioner according to an embodiment.

Figure 4:
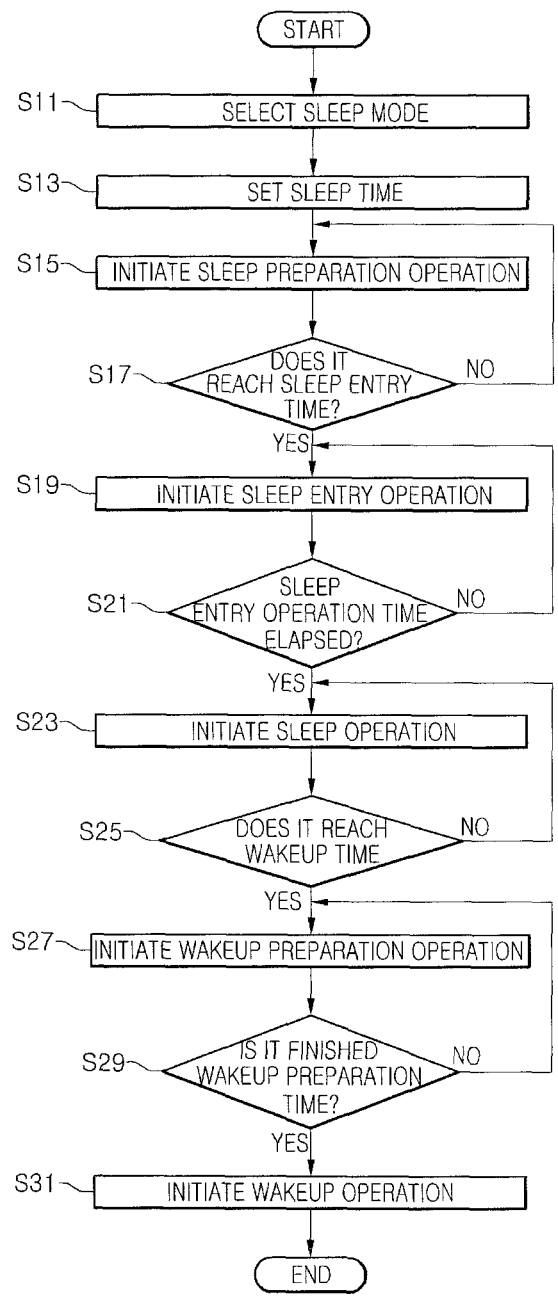
FIG. 4 is a flowchart illustrating a method for controlling an air conditioner according to an embodiment.

FIG. 4 is a flowchart illustrating a method for controlling an air conditioner according to an embodiment.

Referring to FIG. 4, the input unit 130 receives a signal for selecting a sleep mod (S11). The input unit 130 further receives signals for setting a sleep time including a sleep entry time and a wakeup time (S13).

Meanwhile, when the input unit 130 receives the signals for selecting the sleep mode and setting the sleep entry time and wakeup time, the control unit 140 controls such that the lighting unit 120 performs the sleep preparation operation (S15). Accordingly, the indoor space 1 is illuminated to have the first predetermined luminance L1 by light having the first predetermined color temperature K1.

Further, the control unit 140 determines if it reaches the sleep entry time (S17). Next, when it is determined that it reaches the sleep entry time, the control unit 140 controls such that the lighting unit 120 performs the sleep entry operation (S19). Accordingly, the indoor space 1 is illustrated by light having the first predetermined color temperature K for a predetermined time. At this point, the luminance of the indoor space 1 is gradually reduced from the first predetermined luminance L1 to the second predetermined luminance L2 for the sleep entry operation time.

The control unit 140 determines if the sleep entry operation time has elapsed (S21). When it is determined that the sleep entry operation time has elapsed, the control unit 140 controls such that the lighting unit 120 performs the sleep operation (S23). Therefore, the indoor space 1 is illustrated to have the second predetermined luminance by the light having the first predetermined color temperature K1.

Next, the control unit 140 determines if it reaches the wakeup time (S25). When it is determined that it reaches the wakeup time, the control unit 140 controls such that the lighting unit performs the wakeup preparation operation (S27). Therefore, the indoor space 1 is illuminated by the light having the second predetermined color temperature K2. At this point, the luminance of the indoor space 1 is gradually increased from the second predetermined luminance L2 to the third predetermined luminance L3.

Further, the control unit 140 determines if the wakeup preparation operation time has elapsed (S29). When it is determined that the wakeup preparation operation time has elapsed, the control unit 140 controls such that the lighting unit 120 performs the wakeup operation (S31). Therefore, the indoor space 1 is illuminated to have the third predetermined luminance L3 by light having the second predetermined color temperature K2.

In the above-described embodiments, the lighting unit includes the red, green, and blue lighting sources or the first and second lighting sources. However, the present invention is not limited to this. Any lighting sources that can generate light having the first and second predetermined color temperatures may be used.

According to the air conditioners and methods for controlling the air conditioners of the embodiments, the following effects can be expected.

First, the air conditioner may have a variety of functions in accordance with the user's requirements.

As the lighting unit illuminates the indoor space with proper light, the user can efficiently get the sleep and wakeup.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An air conditioner comprising:
an air-conditioning unit comprising a variety of components for air-conditioning of an indoor space;
an lighting unit for illuminating the indoor space;
an input unit receiving signals for operating the air-conditioning unit and signals for selecting a sleep mode; and
a control unit controlling such that, when the input unit receives the signal for selecting the sleep mode, the lighting unit sequentially performs a sleep entry operation where the indoor space is illuminated to have a predetermined sleep entry luminance by light having a predetermined sleep entry color temperature for a predetermined sleep entry operation time, a sleep operation where the indoor space is illuminated to have a predetermined sleep luminance by light having a predetermined sleep color temperature unit it reaches a predetermined wakeup time, and a wakeup operation where the indoor space is illuminated to have a predetermined wakeup luminance by light having a predetermined wakeup color temperature.

2. The air conditioner according to claim 1, wherein the wakeup color temperature is higher than the sleep entry color temperature and the sleep color temperature.

3. The air conditioner according to claim 1, wherein the sleep entry color temperature and the sleep color temperature are 2000-4000K; and
the wakeup color temperature is 4000-6000K.

4. The air conditioner according to claim 1, wherein the sleep luminance is lower than the sleep entry luminance and the wakeup luminance is higher than the sleep entry luminance.

5. The air conditioner according to claim 1, wherein the sleep entry luminance is gradually reduced until the luminance reaches the sleep luminance for the sleep entry operation time.

6. The air conditioner according to claim 1, wherein the sleep entry luminance is 1-100 Lux;
the sleep luminance is 0.01-1 Lux; and
the wakeup luminance is 10-1000 Lux.

7. The air conditioner according to claim 1, wherein, when the input unit receives the signal for selecting the sleep mode, the control unit controls such that the lighting unit performs a sleep preparation operation where the indoor space is illuminated to have a predetermined sleep preparation luminance by light having a predetermined sleep preparation color temperature.

8. The air conditioner according to claim 7, wherein the sleep preparation color temperature and the sleep preparation luminance are same as the sleep entry color temperature and the sleep entry luminance, respectively; and
the sleep entry luminance is gradually reduced from the sleep preparation luminance for the sleep entry operation time.

9. The air conditioner according to claim 7, wherein the sleep preparation color temperature and the sleep entry color temperature is 3000K.

10. The air conditioner according to claim 7, wherein the sleep entry preparation luminance is 1-100 Lux; and
the sleep luminance is 0.01-1 Lux.

11. The air conditioner according to claim 1, wherein, when the input unit receives the signal for selecting the sleep mode, the control unit controls such that the lighting unit performs a
wakeup preparation operation where the indoor room is illuminated to have a predetermined wakeup preparation luminance by light having a predetermined wakeup preparation color temperature for a predetermined wakeup preparation operation time.

12. The air conditioner according to claim 11, wherein the wakeup preparation color temperature is same as the wakeup color temperature; and
the wakeup preparation luminance is gradually increased from the sleep luminance to the wakeup luminance for the wakeup preparation operation time.

13. The air conditioner according to claim 11, wherein the wakeup preparation color temperature and the wakeup color temperature are 5000K.

14. The air conditioner according to claim 11, wherein the sleep luminance is 0.01-1 Lux; and
the wakeup luminance is 10-1000 Lux.

15. The air conditioner according to claim 1, wherein the lighting unit comprises red, green, and blue lighting sources that emit light having the sleep entry color temperature, sleep color temperature, and wakeup color temperature in accordance with a ratio of red, green, blue values.

16. The air conditioner according to claim 1, wherein the lighting unit comprises a plurality of lighting sources emitting light having the sleep entry color temperature, sleep color temperature, and wakeup color temperature.

17. A method for controlling an air conditioner, comprising:
allowing a lighting unit to illuminate an indoor space with a first predetermined luminance using light having a first predetermined color temperature;
allowing the lighting unit to illuminate the indoor space using light having the first predetermined color temperature such that a luminance is gradually reduced from the first predetermined luminance to a second predetermined luminance;

allowing the lighting unit to illuminate the indoor space with the second predetermined luminance using light having the first predetermined color temperature; and allowing the lighting unit to illuminate the indoor space using light having a second predetermined color temperature such that a luminance is gradually increased from the second predetermined luminance to a third predetermined luminance.

18. The method according to claim 17, wherein the first predetermined color temperature is lower than the second predetermined color temperature; and the first predetermined luminance is higher than the second predetermined luminance but lower than the third predetermined luminance.

19. The method according to claim 17, wherein the first predetermined color temperature is 2000-4000K; and the second predetermined color temperature is 4000-6000K.

20. The method according to claim 17, wherein the first predetermined luminance is 1-100 Lux;

the second predetermined luminance is 0.01-1 Lux; and the third predetermined luminance is 10-1000 Lux.

* * * * *